United States Patent [19]

Wampler

[11] Patent Number: 4,906,229

[45] Date of Patent: Mar. 6, 1990

[54] HIGH-FREQUENCY TRANSVALVULAR AXISYMMETRIC BLOOD PUMP

[75] Inventor: Richard K. Wampler, Rancho Cordova, Calif.

[73] Assignee: Nimbus Medical, Inc., Rancho Cordova, Calif.

[21] Appl. No.: 189,527

[22] Filed: May 3, 1988

[51] Int. Cl.⁴ .............................................. A61M 1/10
[52] U.S. Cl. ................................ 600/16; 128/DIG. 3; 417/478; 417/480
[58] Field of Search ..................... 600/16–18; 128/DIG. 3; 417/384–385, 388, 394, 474, 478–480

[56] References Cited

U.S. PATENT DOCUMENTS

| | | | |
|---|---|---|---|
| 3,099,260 | 7/1963 | Birtwell | 600/17 |
| 4,080,958 | 3/1978 | Bregman et al. | 600/16 |
| 4,250,872 | 2/1981 | Tamari | 600/16 |
| 4,465,063 | 8/1984 | Nielsen et al. | 600/16 |
| 4,625,712 | 12/1986 | Wampler | 600/16 |

FOREIGN PATENT DOCUMENTS 0209070 1/1987 European Pat. Off. .

*Primary Examiner*—Angela D. Sykes
*Attorney, Agent, or Firm*—Weissenberger & Peterson

[57] ABSTRACT

A high-frequency transvalvular blood pump for temporary cardiac assist provides suction to decompress the ventricular cavity during both systole and diastole. The intake end of the pump is connected to a cannula which is inserted into the ventricular cavity through the aortic valve, and which has an intake opening at its distal end. The intake and outflow ends of the pump are closed, respectively, by one-way valves which allow blood flow only in the direction of body perfusion. The pump itself consists of a stiff barrel whose interior volume can be alternately reduced and expanded by a flexible membrane controlled by pneumatic or hydraulic pressure from an extracorporeal location through a percutaneously inserted lumen.

7 Claims, 2 Drawing Sheets

HIGH-FREQUENCY TRANSVALVULAR AXISYMMETRIC BLOOD PUMP

FIELD OF THE INVENTION

This invention relates to temporary cardiac assist devices, and more particularly, to a transvalvular blood pump of the balloon type which decompresses the ventricular cavity to maintain blood flow during diastole as well as during systole.

BACKGROUND OF THE INVENTION

Published European Patent Application No. 0209070 of Param J. Singh discloses a high-frequency intra-arterial cardiac support system in which a balloon pump is positioned in a major artery downstream of the heart and is cyclically inflated and deflated at a frequency at least three times that of the normal heartbeat. When inflated during diastole, the Singh balloon pushes blood through the coronary artery. During systole, however, the high impedance of the coronary artery essentially eliminates this effect while the body is being actively perfused.

The Singh balloon does not actively perfuse the body when it is deflated during diastole, as its deflation does not cause any suction through the aortic valve. In order to achieve good myocardial preservation, it is however important to decompress the ventricular cavity during diastole, i.e. to create suction through the aortic valve by the operation of the cardiac assist device.

SUMMARY OF THE INVENTION

The invention overcomes the deficiencies of the prior art by providing a pneumatically or hydraulically operated valved intravascular pump which alternately draws blood from the ventricular cavity through the aortic valve when deflated, and pumps that blood into the body when inflated, during both systole and diastole. Typically, the pump of this invention operates at frequencies on the order of 600 to 1,000 cycles per minute, depending on the size of the stroke. The operability of the pump during both systole and diastole increases its blood throughput by 40–50% over prior art devices.

Because it provides continuous decompression of the ventricular cavity, the pump of this invention does not require any synchronization with the natural heartbeat, as is required by most prior art balloon pumps and is desirable in the Singh pump. This is not only a crucial point in the event of arrythmia, but it also greatly simplifies the pump mechanism and makes its operation easier and more reliable. Also, it dispenses with the need for an EKG or aortic pressure trace, and cardiac assist can thus be initiated with less delay in emergency situations.

The pump of this invention physically consists of an elongated stiff barrel, open at both ends, which is placed in the aorta. The intake end of the barrel is sealingly connected to an intake cannula which extends through the aortic valve and has an intake opening in the ventricular cavity. The intake and outflow ends of the barrel are closed off by flexible one-way valves which allow blood flow only in the direction of body perfusion.

A flexible, resilient membrane generally coextensive with the barrel is mounted on the inside of the barrel wall and is sealingly attached thereto along the periphery of both ends of the barrel. An appropriate conduit extending percutaneously to a pumping apparatus outside the body is arranged to alternately introduce a gaseous or liquid operating fluid into, and evacuate it from, the space between the barrel wall and the membrane.

As the operating fluid is introduced and evacuated, the membrane alternately reduces and expands the volume of the pumping chamber defined by the inside surface of the membrane between the one-way valves. This action alternately draws blood from the ventricular cavity through the intake cannula and the intake valve, and pushes it into the aorta through the outflow valve.

The above-described axisymmetric construction of the pump of this invention has yet another advantage: Because prior art balloon pumps inherently expand to the diameter of the blood vessel in which they are located, they occlude the blood flow during systole as much as ten times per second. Occlusion during systole, however, produces hemolysis; and in addition, the high-frequency pull on the aortic valve caused by prior art pumps can be damaging to the aortic valve.

In the inventive pump, occlusion is prevented both by the fact that the barrel is of smaller diameter than the aorta, so that blood can flow around it, and by so operating the flexible membrane that it stops short of occluding the passage through the barrel during inflation. Any high-frequency pull on the aortic valve is avoided by the transvalvular position of the intake cannula.

It is thus the object of the invention to provide a highfrequency blood pump for cardiac assist which is capable of decompressing the ventricular cavity during both systole and diastole.

It is another object of the invention to provide a highfrequency blood pump for cardiac assist which does not require synchronization with the natural heartbeat.

It is a further object of the invention to provide a highfrequency blood pump for cardiac assist which does not, during systole, occlude the blood vessel in which it is located, and which does not place any high-frequency stress on the aortic valve.

DESCRIPTION OF THE PREFERRED EMBODIMENT

Figure 1:
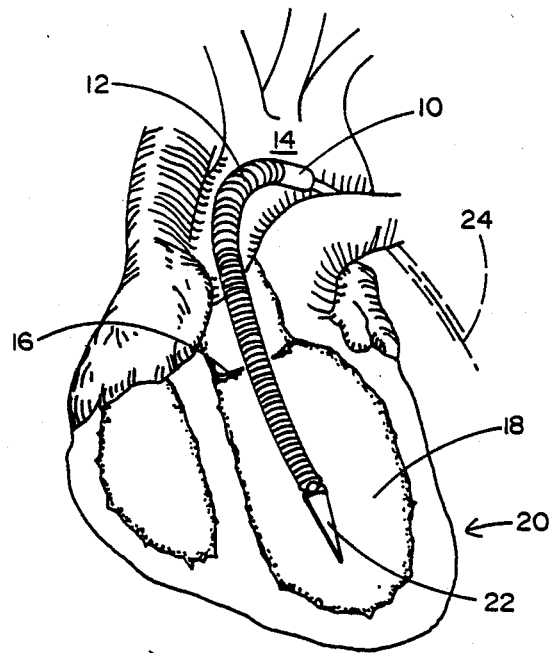
FIG. 1 is a schematic representation of a portion of the human heart and aorta, showing the placement of the device of this invention.

FIG. 1 illustrates the use of the invention in temporary cardiac assist. The high-frequency pump 10, with its intake cannula 12, is inserted percutaneously by conventional means into, e.g., the femoral artery (not shown), and is then pushed up through the femoral artery into the aorta 14 until the distal end of the cannula 12 penetrates through the aortic valve 16 into the ventricular cavity 18 of the heart 20.

The intake cannula 12 may be of any appropriate construction such as, for example, that shown in my copending application Ser. No. 129,713, filed 07 Dec. 1987. The cannula 12 is sealingly attached to the intake end of pump 10 and has an intake opening 22 at its distal end which, during operation of the pump 10 is located in the ventricular cavity 18.

An operating fluid supply lumen 24 extends from the pump 10 through the aorta, femoral artery, and percutaneous insertion point to an appropriate extracorporeal control device (not shown) which alternately injects operating fluid into the lumen 24, and evacuates it therefrom. The operating fluid may be gaseous or liquid, helium being preferred because of its chemical and physical properties. The rate of alternation between the pressurizing and the evacuation of the lumen 24 depends on the volume of blood displaced on each stroke of the pump 10. Typically, for a 5cc stroke, the frequency might be about 600 cyles/minute, and for a 3cc stroke, it might be about 1,000 cycles/minute.

Figure 2:
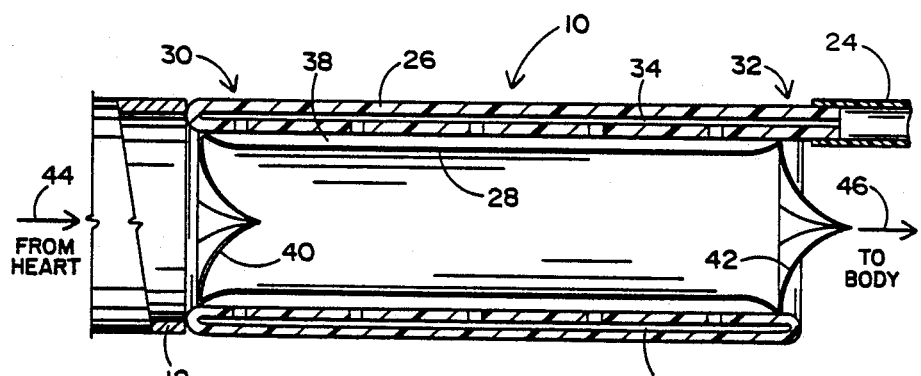
FIG. 2 is an axial section of the pump of this invention.

FIG. 2 shows, somewhat schematically, the internal construction of the pump 10. A cylindrical barrel 26 of stiff, biocompatible plastic material forms the housing of the pump 10. A cylindrical flexible, elastic membrane 28 is sealingly circumferentially attached to the inside wall of barrel 26 at its intake end 30 and at its outflow end 32. A plenum 34 in the wall of barrel 26 conveys operating fluid between the lumen 24 and the space 38 separating the membrane 28 from the inner wall of barrel 26.

A one-way intake valve 40 and a one-way outflow valve 42 are sealingly circumferentially attached to the inside wall of barrel 26 at its intake end 30 and its outflow end 32, respectively. The valves 40, 42 are preferably similar in construction to the natural aortic valve 16 (FIG. 1) and are so oriented as to freely allow blood flow through the barrel 26 in the direction of arrows 44, 46, but to block any blood flow through the barrel 26 in the opposite direction.

Figure 3:
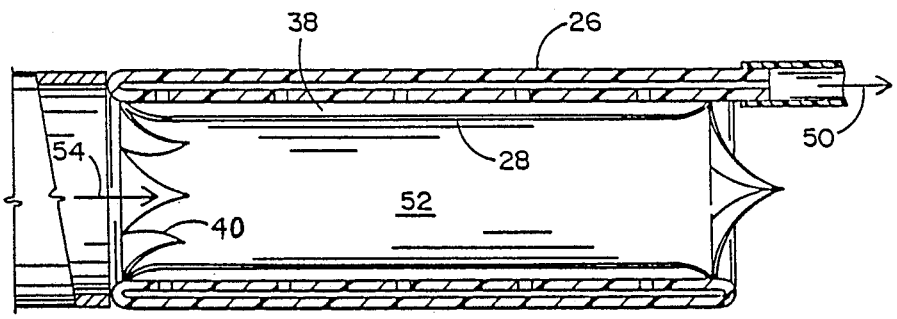
FIG. 3 is a diagrammatic view illustrating the position of the elements of the pump of FIG. 2 following evacuation.
Figure 4:
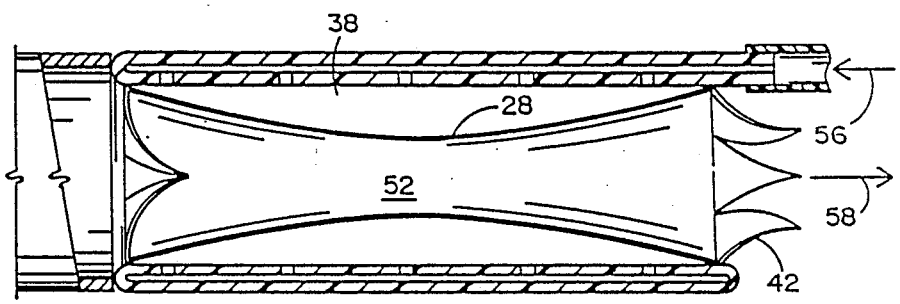
FIG. 4 is a diagrammatic view illustrating the position of the elements of the pump of FIG. 2 following inflation.

The operation of the pump 10 is illustrated diagrammatically in FIGS. 3 and 4. When operating fluid is exhausted from the space 38 as indicated by arrow 50 (FIG. 3), the membrane 28 is drawn against the wall of barrel 26 so as to expand the pumping chamber 52 and draw blood into it from the ventricular cavity 18 (FIG. 1) through cannula 12 and the intake valve 40 which is opened by the blood flow (arrow 54). The outflow valve 42 is closed by the back pressure created by the expansion of chamber 52 and prevents blood from being drawn into the chamber 52 from the direction of the body.

When operating fluid under pressure is introduced into the space 38 as indicated by arrow 56 (FIG. 4), the membrane 28 acts to reduce the volume of chamber 52, and blood is expelled from chamber 52 through the now opening outflow valve 42 toward the body (arrow 58). In order to prevent hemolysis, the movement of membrane 28 is restricted so that the membrane 28 never fully occludes blood passage through the chamber 52.

If the natural blood pressure during systole is high enough, intake valve 40 and outflow valve 42 may both remain open to some degree throughout the pumping cycle and convey additional blood through the chamber 52 toward the body.

It will be noted that inasmuch as the intake opening 22 of cannula 12 is located in the ventricular cavity 18, the operation of the pump 10 does not affect the natural operation of the aortic valve 16, yet provides pulsating suction to decompress the ventricular cavity 18 both during systole and diastole. This is important for good myocardial preservation, and in addition the continual operation of the pump throughout the coronary cycle considerably increases the blood throughput of the vascular system as compared to prior art cardiac assist devices.

I claim:
1. A high-frequency transvalvular blood pump, comprising:
    (a) a substantially cylindrical, stiff barrel dimensioned to be inserted into a blood vessel of a patient and having an outer diameter substantially less than that of said blood vessel, said barrel having an intake end and an outflow end;
    (b) a cannula for insertion into a ventricular cavity through a heart valve, said cannula having a distal and a proximal end and being sealingly joined at said proximal end to said intake end in fluid communication with the interior of said barrel, and said cannula having an intake opening at said distal end for intake of blood from said ventricular cavity when inserted therein;
    (c) fluid-operated pumping means in said barrel for alternately drawing blood into the interior of said barrel and expelling it therefrom, the frequency of alternation of said pumping means being substantially 600 to 1000 cycles per minute; and
    (d) valving means at each end of said barrel for allowing blood flow into and out of said barrel only in the direction from said cannula to said outflow end.

2. The blood pump of claim 1, in which said barrel includes means for conveying operating fluid to and from the outside of the body of said patient, and said pumping means include:
    (i) a substantially cylindrical, flexible membrane sealingly circumferentially attached to said barrel to define a space between the interior wall of said barrel and said membrane; and
    (ii) means for alternatingly introducing and evacuating operating fluid into and from said space so as to alternatingly cause said membrane to reduce and expand the volume defined by the interior surface of said membrane between said valving means.

3. The blood pump of claim 2, in which said operating fluid is a gas.

4. The blood pump of claim 3, in which said operating fluid is helium.

5. The blood pump of claim 2, in which the movement of said membrane is restricted so as to prevent occlusion of the fluid path between said valving means.

6. A method of providing to a patient cardiac assist with good myocardial preservation, comprising the steps of:
    (a) introducing into a major blood vessel adjacent the patient's heart a pulsatile pumping device having an intake end and an outflow end;
    (b) positioning said device so that its intake and outflow ends are located on opposite sides of a heart valve; and
    (c) operating said device so as to produce a pulsatile blood flow having a frequency of substantially 600–1000 cycles per minute through said device across said heart valve during both systole and diastole;
    (d) said device being non-occluding and being of a size sufficiently small to allow substantial blood flow through said blood vessel exteriorly of said device.

7. The method of claim 6, in which said device is operated by a fluid supplied from outside the patient's body through said blood vessel.

* * * * *